United States Patent
Camacho et al.

(10) Patent No.: US 7,167,742 B2
(45) Date of Patent: *Jan. 23, 2007

(54) UTILIZATION OF AN INFRARED PROBE TO DISCRIMINATE BETWEEN MATERIALS

(75) Inventors: Nancy P. Camacho, Edison, NJ (US); Mathias P. G. Bostrom, Scarsdale, NY (US); Steve L. Bertha, New York, NY (US)

(73) Assignee: Hospital for Special Surgery, New York, NY (US)

(*) Notice: Subject to any disclaimer, the term of this patent is extended or adjusted under 35 U.S.C. 154(b) by 988 days.

This patent is subject to a terminal disclaimer.

(21) Appl. No.: 10/142,003

(22) Filed: May 9, 2002

(65) Prior Publication Data

US 2002/0169379 A1 Nov. 14, 2002

Related U.S. Application Data

(60) Provisional application No. 60/289,984, filed on May 10, 2001.

(51) Int. Cl.
*A61B 6/00* (2006.01)
(52) U.S. Cl. .................. 600/473; 600/475; 600/476; 600/477; 600/478; 600/310; 600/312; 250/330; 250/331; 250/332; 250/333; 250/334; 250/317.1
(58) Field of Classification Search ............. 600/476, 600/473, 475, 477, 478; 250/341.2
See application file for complete search history.

(56) References Cited

U.S. PATENT DOCUMENTS 3,769,963 A 11/1973 Goldman et al.

(Continued)

FOREIGN PATENT DOCUMENTS

DE 19841217 A1 4/1999

(Continued)

OTHER PUBLICATIONS

*Infrared and Raman Spectroscopy of Biological Materials*, Eds. Gremlich, H.U., Yar., 3., New York, Marcel-Dekker, pp. 323-377 (2001).

(Continued)

*Primary Examiner*—Brian L. Casler
*Assistant Examiner*—James Kish
(74) *Attorney, Agent, or Firm*—Frishauf, Holtz, Goodman & Chick, P.C.

(57) ABSTRACT

A method of evaluating the surface of a material that has a distinguishable infrared spectrum comprising (a) positioning an infrared fiber optic probe to be in contact with a surface of the sample or material at a region of interest for detecting attenuated total reflectance or within a sufficient distance from the surface of the region for detecting reflection, (b) detecting mid- or near-infrared radiation attenuated total reflectance or reflection off of the surface of the sample or the material, (c) analyzing the infrared radiation from step (b) for at least one of peak height, peak area, frequency and chemometric parameters, and (d) actuating the removal device when a signal from the infrared fiber optic probe is between pre-selected values for at least one of peak height, peak area, frequency and chemometric parameters for the sample of the material.

31 Claims, 1 Drawing Sheet

U.S. PATENT DOCUMENTS

| | | | |
|---|---|---|---|
| 3,941,122 A * | 3/1976 | Jones | 606/128 |
| 4,336,809 A | 6/1982 | Clark | |
| 4,588,885 A | 5/1986 | Lovoi et al. | |
| 4,733,660 A | 3/1988 | Itzkan | |
| 4,737,628 A | 4/1988 | Lovoi | |
| 4,973,848 A * | 11/1990 | Kolobanov et al. | 250/458.1 |
| 5,038,039 A | 8/1991 | Wong et al. | |
| 5,170,056 A | 12/1992 | Berard et al. | |
| 5,197,470 A | 3/1993 | Helfer et al. | |
| 5,204,517 A * | 4/1993 | Cates et al. | 134/1 |
| 5,275,594 A * | 1/1994 | Baker et al. | 606/12 |
| 5,280,788 A | 1/1994 | Janes et al. | |
| 5,281,798 A * | 1/1994 | Hamm et al. | 250/205 |
| 5,286,947 A | 2/1994 | Clyde et al. | |
| 5,304,173 A | 4/1994 | Kittrell et al. | |
| 5,346,488 A | 9/1994 | Prince et al. | |
| 5,452,716 A | 9/1995 | Clift | |
| 5,460,182 A | 10/1995 | Goodman et al. | |
| 5,516,043 A | 5/1996 | Manna et al. | |
| 5,527,273 A | 6/1996 | Manna et al. | |
| 5,596,992 A | 1/1997 | Haaland et al. | |
| 5,701,913 A | 12/1997 | McPherson et al. | |
| 5,733,739 A | 3/1998 | Zakim et al. | |
| 5,746,736 A | 5/1998 | Tankovich | |
| 5,762,609 A | 6/1998 | Benaron et al. | |
| 5,769,791 A | 6/1998 | Benaron et al. | |
| 5,772,597 A | 6/1998 | Goldberger et al. | |
| 5,785,658 A | 7/1998 | Benaron et al. | |
| 5,807,261 A | 9/1998 | Benaron et al. | |
| RE36,044 E | 1/1999 | Benaron | |
| 5,876,397 A | 3/1999 | Edelman et al. | |
| 5,923,808 A | 7/1999 | Melling | |
| 5,986,770 A | 11/1999 | Hein et al. | |
| 5,987,346 A | 11/1999 | Benaron et al. | |
| 6,036,667 A | 3/2000 | Manna et al. | |
| 6,063,050 A | 5/2000 | Manna et al. | |
| 6,068,604 A | 5/2000 | Krause et al. | |
| 6,135,774 A | 10/2000 | Hack et al. | |
| 6,200,307 B1 | 3/2001 | Kasinkas et al. | |
| 6,270,471 B1 | 8/2001 | Hechl et al. | |
| 6,324,419 B1 | 11/2001 | Guzelsu et al. | |
| 6,934,576 B1 * | 8/2005 | Camacho et al. | 600/473 |
| 2001/0048077 A1 | 12/2001 | Afanassieva | |
| 2002/0002336 A1 | 1/2002 | Marchitto et al. | |
| 2002/0010400 A1 | 1/2002 | Camacho et al. | |

FOREIGN PATENT DOCUMENTS

WO     WO 01/87040 A2     11/2001

OTHER PUBLICATIONS

Camacho, N.P., Hou, L., Toledano, T.R., Ilg, W.A., Brayton, C.F., Raggio, C.L., Root, L., and Boskey, A.L., "The Material Basis for Reduced Mechanical Properties in Oim Mice Bones", *J. Bone Miner, Res.*, 14, pp. 264-272, (1999).

Lazarev, Y.A., Grishkovsky, B.A., and Khromova, T.B., "Amide I Band of IR Spectrum and Structure of Collagen and Related Polypeptides", *Biopolymers*, 24, pp. 1449-1478. (1985).

Liu, K.Z., Dembinski, T.C., and Mantsch, H.H., "Rapid Determination of Fetal Lung Maturity from Infrared Spectra of Amniotic Fluid ", *Am. J. Obstet. Gynecol.*, 178, pp. 234-241, (1998).

Mendelsohn, R., and Moore, D.J., "Vibrational Spectroscopic Studies of Lipid Domains in Biomembranes and Model Systems", *Chem. Phys. Lipids*, 96, pp. 141-157, (1998).

Moore, D.J., Rerek, M.E., and Mendelsohn, R., "Lipid Domains and Orthorhombic Phases in Model Stratum Corneum: Evidence from Fourier Transform Infrared Spectroscopy Studies", *Biochem. Biophys. Res. Commun.*, 231, pp. 797-801, (1997).

Moore, D.J., Gioioso, S., Sills, R.H., and Mendelsohn, R., "Some Relationships Between Membrane Phospholipid Domains, Conformational Order, and Cell Shape in Intact Human Erythrocytes", *Biochim. Biophys. Acta.*, 1415, pp. 342-348, (1999).

Paschalis, E.P., Betts, F., DiCarlo, E., Mendelsohn, R., and Boskey, A.L., "FTIR Microspectroscopic Analysis of Normal Human Cortical and Trabecular Bone", *Calcif, Tissue Int.*, 61, pp. 480-486, (1997).

Paschalis, E.P., Betts, F., DiCarlo, E., Mendelsohn, R., and Boskey, A. L., "FTIR Microspectroscopic Analysis of Human Iliac Crest Biopsies from Untreated Osteoporotic Bone", *Calcif. Tissue Int.*, 61, pp. 487-492, (1997).

Camacho, N.P., Landis, W.J., and Boskey, A.L., "Mineral Changes in a Mouse Model of Osteogenesis Imperfecta Detected by Fourier Transform Infrared Microscopy", *Connect. Tissue Res.*, 35, pp. 259-265, (1996).

Camacho, N.P., Rimnac, C.M., Meyer, R.A.J., Doty, S., and Boskey, A.L., "Effect of Abnormal Mineralization on the Mechanical Behavior of X-Linked Hypophosphatemic Mice Femora", *Bone*, 17, pp. 271-278, (1995).

Gadaleta, S.J., Camacho, N.P., Mendelsohn, R., and Boskey, A.L., "Fourier Transform Infrared Microscopy of Calcified Turkey Leg Tendon", *Calcif. Tissue Int.*, 58, pp. 17-23, (1996).

Boskey, A.L., Guidon, P., Doty, S.B., Stiner, D., Leboy, P., and Binderman, I., "The Mechanism of Beta-Glycerophosphate Action in Mineralizing Chick Limb-Bud Mesenchymal Cell Cultures", *J. Bone Miner. Res.*,11, pp. 1694-1702, (1996).

Kidder, L.H., Kalasinsky, V.F., Luke, J.L., Levin, I.W., and Lewis, E.N., "Visualization of Silicone Gel in Human Breast Tissue Using New Infrared Imaging Spectroscopy", *Nat. Med.*, 3, pp. 235-237, (1997).

Lewis, E.N., Kidder, L.H., Levin, I.W., Kalasinsky, V.F., Hanig, J.P., and Lester, D.S., "Applications of Fourier Transform Infrared Imaging Microscopy in Neurotoxicity", *Ann. N.Y. Acad., Sci.*, 820, pp. 234-247, (1997).

Marcott, C., Reeder, R.C., Paschalis, E.P., Tatakis, D.N., Boskey, A.L., and Mendelsohn, R., "Infrared Microspectroscopic Imaging of Biomineralized Tissues Using a Mercury-Cadmium-Telluride Focal-Plane Array Detector", *Cell. Mol. Biol. (Noisy-le-grand)*, 44, pp. 109-115, (1998).

Camacho, N.P., Mendelsohn, R., Grigiene, R., Torzilla, P.A., "Polarized FI-IR Microscopic Determination of Collagen Orientation in Articular Cartilage", 42nd Annual Meeting, Orthopaedic Research Society, Feb. 19-22, 1996, Atlanta, Georgia.

Camacho, N.P., West, P., Torzilli, P.A., Mendelsohn, R., "FTIR Microscopic Imaging of Collagen and Proteoglycan in Bovine Cartilage", *Biopolymers*, 62:1-8 (2001).

Potter, K., Kidder, L.H., Levin, I.W., Lewis E.N., Spencer R.G., "Imaging of Collagen and Proteoglycan in Cartilage Sections Using Fourier Transform Infrared Spectral Imaging", *Arthritis & Rheum* 44 (4) :846-855 (2001).

Schumacher, H.R., Klippel, J.H., and Koopman, W.J., "Articular Cartilage", *Primer on the Rheumatic Diseases*, 11th edition, Atlanta: The Arthritis Foundation, pp. 14-18, (1993).

Horecker, B., Kaplan, N.O., Marmur, J., and Scheraga, H.A., "Collagens", *Conformation in Fibrous Proteins and Related Synthetic Polypeptides*, New York: Academic Press, editors Fraser, R.D.B. and MacRae, T.P., pp. 344-402, (1973).

George, A., and Veis, A., "FTIRS in $H_2$ O Demonstrates that Collagen Monomers Undergo a Conformational Transition Prior to Thermal Self-Assembly In Vitro", *Biochemistry*, 30, pp. 2372-2377, (1991).

Lazarev, Y.A., Grishkovsky, B.A., Khromova, T.B., Lazareva, A.V., and Grechishko, V.S., "Bound Water in Collagen-Like Triple Helical Structure", *Biopolymers*, 32, pp. 189-195, (1992).

Bychkov, S.M., and Kuzmina, S.A., "Study of Tissue Proteoglycans by Means of Infrared Spectroscopy", *Biull. Eksp. Biol. Med.*, 114, pp. 246-249, (1992).

Bychkov, S.M., Bogatov, V.N., and Kuzmina, S.A., "Infrared Spectra of Cartilage Proteoglycans", *Bull. Eksp. Biol. Med.*, 90, pp. 561-563, (1980).

Bychkov, S.M., Bogatov, V.N., and Kuzmina, S.A., "Study of Different Proteoglycan Salts", *Bull. Eksp. Biol. Med.*, 92, pp. 302-305, (1981).

Buckwalter, J.A., and Mow, V.C., "Injuries to Cartilage and Meniscus: Sports Injuries to Articular Cartilage", DeLee, J.C., and Drez, D., Jr., *Orthopaedic-Sports Medicine Principles and Practice*, Philadelphia: W.B. Saunders Company, pp. 82-107, (1994).

Potter, H.G., Linklater, J.M., Allen, A.A., Hannafin, J.A., and Haas, S.B., "Magnetic Resonance Imaging of Articular Cartilage in the Knee: An Evaluation With Use of Fast-Spin-Echo Imaging", *J. Bone Joint Surg. Am.*, 80, pp. 1276-1284, (1998).

Recht, M.P., and Resnick, D., "Magnetic Resonance Imaging of Articular Cartilage: An Overview" *Top. Magn. Reson. Imaging*, 9, pp. 328-336, (1998).

Speer, D.P., and Dahners, L., "The Collagenous Architecture of Articular Cartilage, Correlation of Scanning Electron Microscopy and Polarized Light Microscopy Observations", *Clin. Orthop.*, 167, 99. 267-275, (1979).

Panula, H.E., Hyttinen, M.M., Arokoski, J.P., Langsjo, T.K., Pelettari, A., Kiviranta, I., and Helminen, H.J., "Articular Cartilage Superficial Zone Collagen Birefringence Reduced and Cartilage Thickness Increased before Surface Fibrillation in Experimental Osteoarthritis", *Ann. Rheum. Dis.*, 57, pp. 237-245, (1998).

Gadaleta, S.J., Landis, W.J., Boskey, A.L., and Mendelsohn, R., "Polarized FT-IR Microscopy of Calcified Turkey Leg Tendon", *Connect. Tissue Reg.*, 34, pp. 203-211, (1996).

Pachalis, E.P., F. Betts, E. DiCarlo, J.M. Lane, R. Mendelsohn, and A.L. Boskey, "Mineral and Organic Matrix Changes in Osteoporosis", *J. Dent. Res.*, 76, p. 287 (1997).

M. Khan, M. Yamauchi, S. Srisawasdi, D. Stiner, S. Doty, E.P. Paschalis, A.L. Boskey, "Homocysteine Decreases Chondrocyte-Mediated Matrix Mineralization In Differentiating Chick Limb-bud Mesenchymal Cell Micro-Mass Cultures", *Bone*, 28, 387-398 (2001).

Hollander, A.P., T.F. Heathfield, C. Webber, Y. Iwata, R. Bourne, C. Rorabeck, and A.R. Poole, (1994), "Increased Damage to Type II Collagen in Osteoarthritic Articular Cartilage Detected by a New Immunoassay", *Journal of Clinical Investigation*, 93, pp. 1722-1732.

Griffiths, P.R., and J.A. de Haseth, (1986), "Fourier Transform Infrared Spectrometry", *Wiley-Interscience*, New York, 457, pp. 188-193.

U.S. Appl. No. 09/853,298, Camacho et al.

Sedel L., (2000), "Evolution of Alumina-on-Alumina Implants: A Review", *Clin. Orthop.*, 48-54.

Santavirta S., Takagi M., Gomez-Barrena E., Nevalainen J., Lassus J., Salo J., et al., (1999), "Studies of Host Response to Orthopedic Implants and Biomaterials", *J. Long Term Eff. Med. Implants.*, 9:67-76.

Behravesh E., Yasko A.W., Engel P.S., Mikos A.G., (1999), "Synthetic Biodegradable Polymers for Orthopaedic Applications", *Clin. Orthop.*, S118-S129.

Khan S.N., Sandhu H.S., Parvataneni H.K., Girardi F.P., Cammisa F.P., (2000), "Bone Graft Substitutes in Spine Surgery", *Bull. Hosp. Jt. Dis.*, 59:5-10.

Willmann G., (2000), "Ceramic Femoral Head Retrieval Data", *Clin. Orthop.*, 22-28.

Bostman O., Pihlajamaki H., (2000), "Clinical Biocompatibility of Biodegradable Orthopaedic Implants for Internal Fixation: A Review", *Biomaterials*, 21:2615-2621.

Fujikawa K., Kobayashi Y., Sasazaki Y., Matsumoto H., Seedhom B.B., (2000), "Anterior Cruciate Ligament Reconstruction with the Leeds-Keio Artificial Ligament", *J. Long Term Eff. Med. Implants*, 10:225-238.

Marti A., (2000), "Cobalt-Base Alloys Used in Bone Surgery", *Injury 31 Suppl.*, 4:18-21.

Pietrzak W.S., (2000), "Principles of Development and Use of Absorbable Internal Fixation", *Tissue Eng.*, 6:425-433.

Cordewener F.W., Schmitz J.P., (2000), "The Future of Biodegradable Osteosyntheses", *Tissue Eng.*, 6:413-424.

Boden S.D., (2000), "Biology of Lumbar Spine Fusion and Use of Bone Graft Substitutes: Present, Future, and Next Generation", *Tissue Eng.*, 6:383-399.

Reddi A.H., (2000), "Morphogenesis and Tissue Engineering of Bone and Cartilage: Inductive Signals, Stem Cells, and Biomimetic Biomaterials", *Tissue Eng.*, 6:351-359.

Hollinger J.O., Winn S., Bonadio J., (2000), "Options for Tissue Engineering to Address Challenges of the Aging Skeleton", *Tissue Eng.*, 6:341-350.

Caplan A.I., (2000), "Tissue Engineering Designs for the Future: New Logics, Old Molecules", *Tissue Eng.*, 6:1-8.

Krejci I., Schupbach P., Balmelli F., Lutz F., (1999), "The Ultrastructure of a Compomer Adhesive Interface in Enamel and Dentin, and its Marginal Adaptation Under Dentinal Fluid as Compared to that of a Composite", *Dent. Mater.*, 15:349-358.

Lutz F., Krejci I., (2000), "Amalgam Substitutes: A Critical Analysis", *J. Esthet. Dent.*, 12:146-159.

Tate W.H., You C., Powers J.M., (2000), "Bond Strength of Compomers to Human Enamel", *Oper. Dent.*, 25:283-291.

Tate W.H., You C., Powers J.M., (1999), "Bond Strength of Copomers to Dentin Using Acidic Primers", *Am. Jour. of Dent.*, vol. 12, No. 5, pp. 235-242.

Attin T., Opatowski A., Meyer C., Zingg-Meyer B., Monting J.S., (2000), "Class II Restorations With a Polyacid-Modified Composite Resin in Primary Molars Placed in a Dental Practice: Results of a Two-Year Clinical Evaluation", *Oper. Dent.*, 25:259-264.

Boskey A.L., Gadaleta S., Gundberg C., Doty S.B., Ducy P., Karsenty G., (1998), "Fourier Transform Infrared Microspectroscopic Analysis of Bones of Osteocalcin-deficient Mice Provides Insight into the Function of Osteocalcin", *Bone.* 23:187-196.

Camacho N.P., Hou L., Toledano T.R., Ilg W.A., Brayton C.F., Raggio C.L., et al., (1999), "The Material Basis for Reduced Mechanical Properties in Oim Mice Bones", *J. Bone Miner. Res.*, 14:264-272.

Paschalis E.P., DiCarlo E., Betts F., Sherman P., Mendelsohn R., Boskey A.L., (1996), "FTIR Microspectroscopic Analysis of Human Osteonal Bone", *Calcif. Tissue Int.*, 59:480-487.

Weng J., Liu Q., Wolke J.G., Zhang X., de Groot K., (1997), "Formation and Characteristics of the Apatite Layer on Plasma-Sprayed Hydroxyapatite Coatings in Simulated Body Fluid", *Biomaterials*, 18:1027-1035.

Shaw R.A., Eysel H.H., Liu K.Z., Mantsch H.H., (1998), "Infrared Spectroscopic Analysis of Biomedical Specimens Using Glass Substrates", *Anal. Biochem.*, 259:181-186.

Rehman I., Knowles J.C., Bonfield W., (1998), "Analysis of *In Vitro* Reaction Layers Formed on Bioglass Using Thin-Film X-Ray Diffraction and ATR-FTIR Microspectroscopy", *J. Biomed. Mater. Res.*, 41:162-166.

Zhang, S.F., Rolfe P., Wright G., Lian W., Milling A.J., Tanaka S., et al., (1998), "Physical and Biological Properties of Compound Membranes Incorporating a Copolymer with a Phosphorylcholine Head Group", *Biomaterials*, 19:691-700

Rehman I., Karsh M., Hench L.L., Bonfield W., (2000), "Analysis of Apatite Layers on Glass-Ceramic Particulate Using FTIR and FT-Raman Spectroscopy", *J. Biomed. Mater. Res.*, 50:97-100.

Collier J.H., Camp J.P., Hudson T.W., Schmidt C.E., (2000), "Synthesis and Characterization of PolypyrroleHyaluronic Acid Composite Biomaterials for Tissue Engineering Applications", *J. Biomed. Mater. Res.*, 50:574-584.

Schultz C.P., Liu K.Z., Kerr P.D., Mantsch H.H., (1998), "In Situ Infrared Histopathology of Keratinization in Human Oral/Oropharyngeal Squamous Cell Carcinoma", *Oncol. Res.*, 10:277-286.

Fukuyama Y., Yoshida S., Yanagisawa S., Shimizu M., (1999), "A Study on the Differences Between Oral Squamous Cell Carcinomas and Normal Oral Mucosas Measured by Fourier Transform Infrared Spectroscopy", *Biospectroscopy*, 5:117-126.

McIntosh L.M., Jackson M., Mantsch H.H., Stranc M.F., Pilavdzic D., Crowson A.N., (1999), "Infrared Spectra of Basal Cell Carcinomas are Distinct from Non-Tumor-Bearing Skin Components", *J. Invest. Dermatol.*, 112:951-956.

Boydston-White S., Gopen T., Houser S., Bargonetti J., Diem M., (1999), "Infrared Spectroscopy of Human Tissue. V. Infrared Spectroscopic Studies of Myeloid Leukemia (ML-1) Cells at Different Phases of the Cell Cycle", *Biospectroscopy*, 5:219-227.

Shaw R.A., Guijon F.B., Paraskevas M., Ying S.L., Mantsch H.H., (1999), "Infrared Spectroscopy of Exfoliated Cervical Cell Specimens, Proceed with Caution", *Anal. Quant. Cytol. Histol.*, 21:292-302.

Hull E.L., Conover D.L., Foster T.H., (1999), "Carbogen-Induced Changes in Rat Mammary Tumour Oxygenation Reported by Near Infrared Spectroscopy", *Br. J. Cancer*, 79:1709-1716.

Quaresima V., Sacco S., Totaro R., Ferrari M., (2000), "Non-invasive Measurement of Cerebral Hemoglobin Oxygen Saturation Using Two Near Infrared Spectroscopy Approaches", *J. Biomed. Opt.*, 5:201-205.

Feng W., Haishu D., Fenghua T., Jun Z., Qing X., Xianwu T., (2001), "Influence of Overlying Tissue and Probe Geometry on the Sensitivity of a Near-Infrared Tissue Oximeter", *Physiol. Meas.*, 22:201-208.

White J.G., (1994), "On-line Moisture Detection for a Microwave Vacuum Dryer", *Pharm. Res.*, 11:728-732.

Blanco M., Coello J., Iturriaga H., Maspoch S., Rovira E., (1997), "Determination of Water in Ferrous Lactate by Near Infrared Reflectance Spectroscopy with a Fibre-Optic Probe", *J. Pharm. Biomed. Anal.*, 16:255-262.

Bouveresse E., Casolino C., de la P.C., (1998), "Application of Standardisation Methods to Correct the Spectral Differences Induced by a Fibre Optic Probe Used For the Near-Infrared Analysis of Pharmaceutical Tablets", *J. Pharm. Biomed. Anal.*, 18:35-42.

Andersson M., Folestad S., Gottfries J., Johansson M.O., Josefson M., Wahlund K.G., (2000), "Quantitative Analysis of Film Coating in a Fluidized Bed Process by In-Line NIR Spectrometry and Multivariate Batch Calibration", *Anal. Chem.*, 72:2099-2108.

Harris S.C., Walker D.S., (2000), "Quantitative Real-Time Monitoring of Dryer Effluent Using Fiber Optic Near-Infrared Spectroscopy", *J. Pharm. Sci.*, 89:1180-1186.

Uemura T., Nishida K., Sakakida M., Ichinose K., Shimoda S., Shichiri M., (1999), "Non-Invasive Blood Glucose Measurement by Fourier Transform Infrared Spectroscopic Analysis Through the Mucous Membrane of the Lip: Application of a Chalcogenide Optical Fiber System", *Front. Med. Biol. Eng.*, 9:137-153.

Dadd M.R., Sharp D.C., Pettman A.J., Knowles C.J., (2000), "Real-Time Monitoring of Nitrile Biotransformations by Mid-Infrared Spectroscopy", *J. Microbiol. Methods*, 41:69-75.

Doak D.L., Phillips J.A., (1999), "*In Situ* Monitoring of an *Escherichia Coli* Fermentation Using A Diamond Composition ATR Probe and Mid-Infrared Spectroscopy", *Biotechnol. Prog.*, 15:529-539.

Camacho N.P., Lin J., Yang X., West P. and Bostrom M.P.G., "An Infrared Fiber Optic Probe for Detection of Degenerative Cartilage", Trans 48th ORS Meeting, 2002 (Abstract).

Paschalis E.P., Jacenko O., Olsen B., Mendelsohn R. and Boskey A.L., "Fourier Transform Infrared Microspectroscopic Analysis Identifies Alterations in Mineral Properties in Bones from Mice Transgenic for Type X Collagen", *Bone*, vol. 19, No. 2, (1996), pp. 151-156.

Boskey A.L., Gadaleta S., Gundberg C., Doty S.B., Ducy P. and Karsenty G., "Fourier Transform Infrared Microspectroscopic Analysis of Bones of Osteocalcin-Deficient Mice Provides Insight Into the Function of Osteocalcin", *Bone*, vol. 23, No. 3, (1998), pp. 187-196.

Paschalis E.P., Jacenko O., Olsen B., deCrombrugghe B., Boskey A.L., (1996), "The Role of Type X Collagen in Endochondral Ossification as Deduced by Fourier Transform Infrared Microscopy Analysis", *Connect. Tissue Res.*, 35:371-377.

Bostrom M.P.G., West P., Yang X., Camacho N.P., "Evaluation of Cartilage Degradation by an Infrared Fiber Optic Probe", presented at the 4th Combined Meeting of the Orthopaedic Research Society, 2001.

US 6,230,044, 05/2001, Afanassieva et al. (withdrawn)

* cited by examiner

UTILIZATION OF AN INFRARED PROBE TO DISCRIMINATE BETWEEN MATERIALS

CROSS REFERENCE TO RELATED APPLICATION

The present application claims the benefit of Provisional Application Ser. No. 60/289,984, filed May 10, 2001, for which priority under 35 USC 119(e) is claimed.

BACKGROUND OF THE INVENTION

1. Field of the Invention

The present invention concerns the application of a probe operative in the mid- or near-infrared ("IR") region of the electromagnetic spectrum ("EM") for in situ sensing of the absorption of infrared energy or reflected infrared energy of a material that has a distinguishable infrared spectrum and removing such material with a combined ablator, cutter, carver or polisher.

More specifically, the present invention concerns the application of a probe operative in the mid- or near-IR region of the EM for in situ sensing of the absorption of infrared energy or reflected infrared energy for distinguishing between two materials that have different infrared spectra and separating or removing one material from the other with an ablator, cutter, carver or polisher.

In a particular embodiment, the present invention relates to the application of a probe operative in the mid- or near-IR region of the EM for in situ sensing of the absorption of infrared energy or reflected infrared energy for (i) discriminating between a host tissue and a non-host material in situ or in vivo, and (ii) in combination with an ablator, cutter, carver or polisher, separating the non-host material from the host tissue in situ or in vivo.

2. Background Information

There is a need for identifying different materials in contact with each other and simultaneously removing one of such materials by, for example, ablation, for example, separating a non-host material from a host material in situ or in vivo, or carving or polishing a resin in the presence of another material.

Advances in biomaterials and tissue engineering have made a significant impact in health care over the last few decades. A multitude of materials or systems that replace or help to regenerate human tissue to restore function have been developed. Materials such as metals, polymers, ceramics, glass, composites and bone substitutes have been implanted primarily for orthopedic applications (Sedel L., (2000), "Evolution of Alumina-on-Alumina Implants: A Review", *Clin. Orthop.*, 48–54; Santavirta S., Takagi M., Gomez-Barrena E., Nevalainen J., Lassus J., Salo J., et al., (1999), "Studies of Host Response to Orthopedic Implants and Biomaterials", *J. Long Term Eff. Med. Implants.*, 9:67–76; Behravesh E., Yasko A. W., Engel P. S., Mikos A. G., (1999), "Synthetic Biodegradable Polymers for Orthopaedic Applications", *Clin. Orthop.*, S118–S129; Khan S. N., Sandhu H. S., Parvataneni H. K., Girardi F. P., Cammisa F. P., (2000), "Bone Graft Substitutes in Spine Surgery", *Bull. Hosp. Jt. Dis.*, 59:5–10; Willmann G., (2000), "Ceramic Femoral Head Retrieval Data", *Clin. Orthop.*, 22–28; Bostman O., Pihlajamaki H., (2000), "Clinical Biocompatibility of Biodegradable Orthopaedic Implants for Internal Fixation: A Review", *Biomaterials*, 21:2615–2621; Fujikawa K., Kobayashi T., Sasazaki Y., Matsumoto H., Seedhom B. B., (2000), "Anterior Cruciate Ligament Reconstruction with the Leeds-Keio Artificial Ligament", *J. Long Term Eff. Med. Implants*, 10:225–238; Marti A., (2000), "Cobalt-Base Alloys Used in Bone Surgery", *Injury* 31 *Suppl.*, 4:18–21). Other bioactive or biodegradable materials, drugs, scaffolds, cells and various synthetic components have been utilized in vivo for many other tissue engineering applications (Pietrzak W. S., (2000), "Principles of Development and Use of Absorbable Internal Fixation", *Tissue Eng.*, 6:425–433; Cordewener F. W., Schmitz J. P., (2000), "The Future of Biodegradable Osteosyntheses", *Tissue Eng.*, 6:413–424; Boden S. D., (2000), "Biology of Lumbar Spine Fusion and Use of Bone Graft Substitutes: Present, Future, and Next Generation", *Tissue Eng.*, 6:383–399; Reddi A. H., (2000), "Morphogenesis and Tissue Engineering of Bone and Cartilage: Inductive Signals, Stem Cells, and Biomimetic Biomaterials", *Tissue Eng.*, 6:351–359; Hollinger J. O., Winn S., Bonadio J., (2000), "Options for Tissue Engineering to Address Challenges of the Aging Skeleton", *Tissue Eng.*, 6:341–350; Caplan A. I., (2000), "Tissue Engineering Designs for the Future: New Logics, Old Molecules", *Tissue Eng.*, 6:1–8). Commensurate with such developments is the requirement for new methodology to evaluate the integration of "non-host" materials into host tissue, to assess their capability for regeneration and repair of the tissue, and to discern between the non-host material and the host tissue in situ.

Although at times it is possible to distinguish the non-host components from host tissues in situ, there are many situations where this is not possible by visual examination alone. One example is the use of bone cement, polymethyl methacrylate ("PMMA"), in orthopaedic surgery. PMMA is utilized frequently to cement components used in joint arthroplasty, such as hip stems, to the bone. When revision surgery is necessary to replace the old hip stem with a new one, it is extremely difficult for the surgeon to visually discern the PMMA from the bone in the femoral canal, and thus to adequately remove it. Another example is the discrimination and/or removal of PMMA cement or fillings from teeth. Although metal fillings can easily be discerned from teeth, it is sometimes difficult to discern non-amalgam-based fillings made of composite materials (Krejci I., Schupbach P., Balmelli F., Lutz F., (1999), "The Ultrastructure of a Compomer Adhesive Interface in Enamel and Dentin, and its Marginal Adaptation Under Dentinal Fluid as Compared to that of a Composite", *Dent. Mater.*, 15:349–358; Lutz F., Krejci I., (2000), "Amalgam Substitutes: A Critical Analysis", *J. Esthet. Dent.*, 12:146–159; Tate W. H., You C., Powers J. M., (2000), "Bond Strength of Compomers to Human Enamel", *Oper. Dent.*, 25:283–291; Attin T., Opatowski A., Meyer C., Zingg-Meyer B., Monting J. S., (2000), "Class II Restorations With a Polyacid-Modified Composite Resin in Primary Molars Placed in a Dental Practice: Results of a Two-Year Clinical Evaluation", *Oper. Dent.*, 25:259–264) or PMMA cement, from the tooth itself. The availability of a technique which could be conveniently utilized in situ to discriminate between a host tissue and a non-host material would be very advantageous for the medical and dental fields.

The techniques of mid- and near-infrared spectroscopy have been utilized extensively in the biomedical field. Mid-infrared spectroscopy has been utilized to study biological molecules (reviewed in "*Infrared and Raman Spectroscopy of Biological Materials*", New York, Marcel Dekker, 2001), including bone (Boskey A. L., Gadaleta S., Gundberg C., Doty S. B., Ducy P., Karsenty G., (1998), "Fourier Transform Infrared Microspectroscopic Analysis of Bones of Osteocalcin-deficient Mice Provides Insight into the Function of Osteocalcin", *Bone.* 23:187–196; Camacho N. P., Rimnac C., Meyer R., Jr., Doty S. Boskey A., (1995), "Effect of Abnormal Mineralization on the Mechanical Behavior of X-Linked Hypophosphatemic Mice Femora", [published erratum appears in *Bone*, July 1996, ] 19(1):77, *Bone*, 17:271–278; Camacho N. P., Landis W. J., Boskey A. L., (1996), "Mineral Changes in a Mouse Model of Osteogenesis Imperfecta Detected by Fourier Transform Infrared Microscopy", *Connect. Tissue Res.*, 35:25–265; Camacho N. P., Hou L., Toledano T. R., Ilg W. A., Brayton C. F., Raggio C. L., et al., (1999), "The Material Basis for Reduced Mechanical Properties in Oim Mice Bones", *J. Bone Miner. Res.*, 14:264–272; Paschalis E. P., DiCarlo E., Betts F., Sherman P., Mendelsohn R., Boskey A. L., (1996), "FTIR Microspectroscopic Analysis of Human Osteonal Bone", *Calcif. Tissue Int.*, 59:480–487; Paschalis E. P., Jacenko O., Olsen B., deCrombrugghe B., Boskey A. L., (1996), "The Role of Type X Collagen in Endochondral Ossification as Deduced by Fourier Transform Infrared Microscopy Analysis", *Connect. Tissue Res.*, 35:371–377; Paschalis E. P., Betts F., DiCarlo E., Mendelsohn R., Boskey A. L., (1997), "FTIR Microspectroscopic Analysis of Normal Human Cortical and Trabecular Bone", *Calcif. Tissue Int.*, 61:480–486) and cartilage (Potter-K., Kidder L. H., Levin I. W., Lewis E. N., Spencer R. G., (2001), "Imaging of Collagen and Proteoglycan in Cartilage Sections Using Fourier Transform Infrared Spectral Imaging", *Arthritis Rheum.*, 44:846–855; Camacho N. P., West P., Torzilli P. A., Mendelsohn R., (2001), "FTIR Microscopic Imaging of Collagen and Proteoglycan in Bovine Cartilage", *Biopolymers*, 62:1–8), for the analysis of the structure and components of biomaterials (Weng J., Liu Q., Wolke J. G., Zhang X., de Groot K., (1997), "Formation and Characteristics of the Apatite Layer on Plasma-Sprayed Hydroxyapatite Coatings in Simulated Body Fluid", *Biomaterials*, 18:1027–1035; Shaw R. A., Eysel H. H., Liu K. Z., Mantsch H. H., (1998), "Infrared Spectroscopic Analysis of Biomedical Specimens Using Glass Substrates", *Anal. Biochem.*, 259:181–186; Rehman I., Knowles J. C., Bonfield W., (1998), "Analysis of In Vitro Reaction Layers Formed on Bioglass Using Thin-Film X-Ray Diffraction and ATR-FTIR Microspectroscopy", *J. Biomed. Mater. Res.*, 41:162–166; Zhang, S. F., Rolfe P., Wright G., Lian W., Milling A. J., Tanaka S., et al., (1998), "Physical and Biological Properties of Compound Membranes Incorporating a Copolymer with a Phosphorylcholine Head Group", *Biomaterials*, 19:691–700; Rehman I., Karsh M., Hench L. L., Bonfield W., (2000), "Analysis of Apatite Layers on Glass-Ceramic Particulate Using FTIR and FT-Raman Spectroscopy", *J. Biomed. Mater. Res.*, 50:97–100; Collier J. H., Camp J. P., Hudson T. W., Schmidt C. E., (2000), "Synthesis and Characterization of PolypyrroleHyaluronic Acid Composite Biomaterials for Tissue Engineering Applications", *J. Biomed. Mater. Res.*, 50:574–584) and recently, has been proposed as a technique to evaluate malignancy in tissue (Schultz C. P., Liu K. Z., Kerr P. D., Mantsch H. H., (1998), "In Situ Infrared Histopathology of Keratinization in Human Oral/Oropharyngeal Squamous Cell Carcinoma", *Oncol. Res.*, 10:277–286; Fukuyama Y., Yoshida S., Yanagisawa S., Shimizu M., (1999), "A Study on the Differences Between Oral Squamous Cell Carcinomas and Normal Oral Mucosas Measured by Fourier Transform Infrared Spectroscopy", *Biospectroscopy*, 5:117–126; McIntosh L. M., Jackson M., Mantsch H. H., Stranc M. F., Pilavdzic D., Crowson A. N., (1999), "Infrared Spectra of Basal Cell Carcinomas are Distinct from Non-Tumor-Baring Skin Components", *J. Invest. Dermatol.*, 112:951–956; Boydston-White S., Gopen T., Houser S., Bargonetti J., Diem M., (1999), "Infrared Spectroscopy of Human Tissue. V. Infrared Spectroscopic Studies of Myeloid Leukemia (ML-1) Cells at Different Phases of the Cell Cycle", *Biospectroscopy*, 5:219–227; Shaw R. A., Guijon F. B., Paraskevas M., Ying S. L., Mantsch H. H., (1999), "Infrared Spectroscopy of Exfoliated Cervical Cell Specimens, Proceed with Caution", *Anal. Quant. Cytol. Histol.*, 21:292–302).

Near-infrared spectroscopy has been used to study hemoglobin oxygen saturation (Hull E. L., Conover D. L., Foster T. H., (1999), "Carbogen-Induced Changes in Rat Mammary Tumour Oxygenation Reported by Near Infrared Spectroscopy", *Br. J. Cancer*, 79:1709–1716; Quaresima V., Sacco S., Totaro R., Ferrari M., (2000), "Non-invasive Measurement of Cerebral Hemoglobin Oxygen Saturation Using Two Near Infrared Spectroscopy Approaches", *J. Biomed. Opt.*, 5:201–205; Feng W., Haishu D., Fenghua T., Jun Z., Qing X., Xianwu T., (2001), "Influence of Overlying Tissue and Probe Geometry on the Sensitivity of a Near-Infrared Tissue Oximeter", *Physiol. Meas.*, 22:201–208), and in conjunction with a fiber optic probe, to study water content and product quality in the pharmaceutical industry (White J. G., (1994), "On-line Moisture Detection for a Microwave Vacuum Dryer", *Pharm. Res.*, 11:728–732; Blanco M., Coello J., Iturriaga H., Maspoch S., Rovira E., (1997), "Determination of Water in Ferrous Lactate by Near Infrared Reflectance Spectroscopy with a Fibre-Optic Probe", *J. Pharm. Biomed. Anal.*, 16:255–262; Bouveresse E., Casolino C., de la P. C., (1998), "Application of Standardisation Methods to Correct the Spectral Differences Induced by a Fibre Optic Probe Used For the Near-Infrared Analysis of Pharmaceutical Tablets", *J. Pharm. Biomed. Anal.*, 18:35–42; Andersson M., Folestad S., Gottfries J., Johansson M. O., Josefson M., Wahlund K. G., (2000), "Quantitative Analysis of Film Coating in a Fluidized Bed Process by In-Line NIR Spectrometry and Multivariate Batch Calibration", *Anal. Chem.*, 72:2099–2108; Harris S. C., Walker D. S., (2000), "Quantitative Real-Time Monitoring of Dryer Effluent Using Fiber Optic Near-Infrared Spectroscopy", *J. Pharm. Sci.*, 89:1180–1186).

To date, mid-infrared fiber optic spectroscopic applications in the biomedical field have been limited, but include non-invasive blood glucose measurement (Uemura T., Nishida K., Sakakida M., Ichinose K., Shimoda S., Shichiri M., (1999), "Non-Invasive Blood Glucose Measurement by Fourier Transform Infrared Spectroscopic Analysis Through the Mucous Membrane of the Lip: Application of a Chalcogenide Optical Fiber System", *Front. Med. Biol. Eng.*, 9:137–153), the study of bio-reactions (Dadd M. R., Sharp D. C., Pettman A. J., Knowles C. J., (2000), "Real-Time Monitoring of Nitrile Biotransformations by Mid-Infrared Spectroscopy", *J. Microbiol. Methods*, 41:69–75; Doak D. L., Phillips J. A., (1999), "In Situ Monitoring of an *Escherichia Coli* Fermentation Using a Diamond Composition ATR Probe and Mid-Infrared Spectroscopy", *Biotechnol. Prog.*, 15:529–539), and most recently, the evaluation of cartilage degradation (Bostrom M. P. G., West P., Yang X., Camacho N. P., "Evaluation of Cartilage Degradation by an Infrared Fiber Optic Probe", presented at the 4th Combined Meeting of the Orthopaedic Research Society, 2001; Camacho N. P., Lin J., Yang X., West P. and Bostrom M. P. G., "An Infrared Fiber Optic Probe for Detection of Degenerative Cartilage", Trans 48th ORS Meeting, 2002 (Abstract)).

The following U.S. patents relate to the selective removal of materials such as paint using laser or other optical energy: U.S. Pat. Nos. 4,588,885; 5,204,517; 5,286,947 and 5,281,798.

The following U.S. patents concern the use of electromagnetic energy to distinguish tissue and involve an ablation, cutting or removal of material: U.S. Pat. Nos. 3,769,963; 4,737,628; 5,197,470; 5,346,488 and 6,200,307.

Lovoi et al. U.S. Pat. No. 4,737,628 concern a method and system for controlled selective removal of material such as a tumor or a substance causing a blood vessel blockage using a "high intensity beam of radiant energy" impinging from a distance to the material to be removed.

Helfer et al. U.S. Pat. No. 5,197,470 concern an instrument and a method for using near IR to discriminate between healthy and diseased tissue using a laser to ablate unwanted tissue, also impinging from a distance to the tissue.

Goldman et al. U.S. Pat. No. 3,769,963 disclose an instrument for performing laser micro-surgery and diagnostic transillumination of tissue such that different wavelengths are used to illuminate different objects or tissue that can then be selectively removed by a surgical laser.

None of the above U.S. patents disclose the use of an infrared fiber optic probe ("IFOP") in contact with a sample or material for detecting its infrared spectrum. Moreover, none of the above U.S. patents disclose an ultrasonic ablator to remove undesired material.

SUMMARY OF THE INVENTION

It is an object of the present invention to utilize IFOP technology to recognize materials that have a distinguishable infrared spectrum and to remove or ablate one such material with an ablator, cutter, carver or polisher.

It is another object of the present invention to utilize IFOP technology to discriminate between two materials that have distinguishable infrared spectrum, e.g., two organic materials, for the purpose of identification and potential removal of one of the materials without removing the other material.

It is a further object of the present invention to utilize IFOP technology to discriminate between two materials, i.e., a host tissue and a non-host material, for the purpose of identification and potential removal of the non-host material in situ.

It is a still further object of the present invention to apply IFOP technology to discriminate between a mineralized tissue, such as bone or teeth, and another compound or material in vivo.

It is a further object of the present invention to employ a probe operative in the mid-infrared region or near-infrared region of the EM for in situ sensing of the absorption of IR energy or of reflected IR energy to discriminate between a mineralized tissue and another compound or material in vivo.

It is a still further object of the present invention to provide a method to discriminate in vivo between bone and bone cement.

It is still another object of the present invention to apply IFOP technology together with an ablation, debridement or cutting system for separating a host tissue in intimate contact with a non-host material.

The present invention relates to a method of evaluating the surface of a material that has a distinguishable infrared spectrum comprising:

(a) positioning an IFOP to be in contact with a surface of a sample or a material at a region of interest for detecting attenuated total reflectance ("ATR") or within a sufficient distance from the surface of the region for detecting reflection, (b) detecting mid- or near-infrared radiation transmitted via ATR or reflection off of the surface of the sample or the material, (c) analyzing the infrared radiation from step (b) for at least one of peak height, peak area, frequency, and chemometric parameters, and (d) actuating a removal device (such as an ablator, cutter, carver or polisher) when a signal from the IFOP is between pre-selected values for at least one of peak height, peak area, frequency and chemometric parameters for the sample or the material.

The present invention is also directed to a method of distinguishing between two materials that have different infrared spectra and separating or removing one material from the other material comprising:

(a) positioning an IFOP to be in contact with a surface of the region of interest for detecting ATR or within a sufficient distance from the surface of the region for detecting reflection, (b) detecting mid- or near-infrared radiation transmitted via ATR or reflection off of the surface of the region of interest, (c) analyzing the infrared radiation from step (b) for at least one peak height, peak area, frequency and chemometric parameters for one or both materials, and (d) actuating a removal device (such as an ablator, cutter, carver or polisher) when a signal from the IFOP is between pre-selected values for at least one of peak height, peak area, frequency and chemometric parameters for one or both materials, or the ratio for at least one of such peak heights, peak areas, frequencies and chemometric parameters for one or both materials, to separate or remove one material from the other material.

The present invention concerns a method for discriminating between a host tissue and a non-host material in vivo comprising:

(a) positioning an IFOP operative in the mid-infrared region or the near-infrared region of the EM to be in contact with a surface of a region of interest where it is considered that a host tissue is in intimate contact with a non-host material for detecting ATR or within a sufficient distance from the surface of the region for detecting reflection, (b) detecting mid-infrared radiation or near-infrared radiation penetrating the surface of the region for detecting ATR or reflection off of the surface of the region for detecting reflection, and (c) analyzing the infrared radiation from step (b) for at least one of peak height, peak area, frequency and chemometric parameters, comparing at least one of peak height, peak area, frequency and chemometric parameters to established values for at least one of peak height, peak area, frequency and chemometric parameters for the host tissue, the non-host material or both the host tissue and the non-host material, to detect the presence or absence of a non-host material.

The present invention also relates to a method for separating a host tissue in intimate contact with a non-host material comprising:

(a) positioning an IFOP operative in the mid-infrared region or the near-infrared region of the EM in combination with a removal device (such as an ablator), the removal device being capable of receiving signals from the IFOP, to be in contact with a surface of a region of interest where it is considered that a host tissue is in intimate contact with a non-host material for detecting ATR or within a sufficient distance from the surface of the region for detecting reflection, (b) detecting with the IFOP mid-infrared radiation or near-infrared radiation penetrating the surface of the region for detecting ATR or reflection off of the surface of the region for detecting reflection, (c) analyzing the infrared radiation from step (b) for at least one of peak height, peak area, frequency and chemometric parameters of the host tissue, the non-host material or both the host tissue and the non-host material, and (d) actuating the removal device (e.g., the ablator, carver or polisher) when a signal from the IFOP is between pre-selected values for (i) at least one of peak height, peak area, frequency and chemometric parameters for one or both of the host tissue and the non-host material, or (ii) the ratio for at least one of the peak heights, peak areas, frequencies and chemometric parameters for one or both of the host tissue and the non-host material.

The present invention also concerns a method of detecting and measuring the thickness of a material in contact with a substrate comprising:

(a) positioning an IFOP operative in the mid-infrared region or the near-infrared region of the EM to be in contact with a surface of a region of interest where it is considered that a surface material is in intimate contact with a substrate for detecting ATR or within a sufficient distance from the surface of the region for detecting reflection, (b) detecting mid-infrared radiation or near-infrared radiation penetrating the surface of the region for detecting ATR or reflection off of the surface of the region for detecting reflection, and (c) analyzing the intensity of the infrared radiation from step (b) for at least one of peak height, peak area, frequency and chemometric parameters to determine and measure the thickness of the surface material.

BRIEF DESCRIPTION OF THE DRAWING

For the purposes of illustrating the invention, there is shown in the drawing a form which is presently preferred. It is to be understood, however, that the present invention is not limited to the precise depiction in the drawing.

DETAILED DESCRIPTION OF THE INVENTION

The present invention involves providing an IFOP which is operative in the mid-infrared region of the EM (approximately 400 $cm^{-1}$ to 5,000 $cm^{-1}$) or in the near infrared region of the EM (approximately 5,000 $cm^{-1}$ to 14,000 $cm^{-1}$).

The probe for use in the present invention can detect infrared radiation by ATR or by reflection. In either case, the evaluation of the region of interest to determine whether it is a host tissue or a non-host material can be carried out by, for example, peak shift analysis, peak area analysis, a combination of peak shift analysis and peak area analysis or by chemometric parameters.

An example of a probe for use in the present invention comprises an ATR element, or can receive reflected IR energy directly, and has an input end and an output end for receiving IR and transmitting attenuated IR radiation, respectively (see U.S. Pat. Nos. 5,170,056 and 5,923,808, the entire contents of both U.S. Pat. Nos. 5,170,056 and 5,923,808 are incorporated by reference herein).

An example of a probe for use in the present invention is as disclosed in U.S. Pat. No. 5,170,056 and is described as follows.

A probe operative in the infrared region of the EM spectrum for in situ real time sensing of the absorption of IR energy in a sample comprising:

an ATR crystal element having an input end portion for receiving IR energy and an output end portion for transmitting attenuated IR energy, the ATR element having wall portions disposed along a central or long axis thereof, the IR energy being reflected along the element in a direction transverse to the central axis;

a plurality of infrared transmitting fibers in the form of a cylindrical bundle at the input end portion and the output end portion of the ATR element, the bundle of fibers having end faces disposed in direct contacting abutment with the ATR element for transmitting and receiving IR energy into and out of the element, the bundle arranged in a cluster of individual fibers, the bundle centered on an axis common with the central axis of the ATR element, the fibers having relatively high numerical apertures for spreading transmitted energy so that a portion of the energy enters the ATR element at an angle less than the critical angle for facilitating total internal reflection by the wall portions of the element and for receiving a sensible amount of IR energy from the ATR element.

In an experimental setup for ATR, the probe is configured with a crystal suitable for ATR such as ZnS. The crystal tip is positioned in optical contact with the surface of the sample. Infrared radiation passes through the surface of the sample, back through the fiber optic and into an infrared detector. This output signal is first measured as a function of the wavelength in the absence of the sample (the background spectrum); and then measured as a function of the wavelength in the presence of the sample. The signal measured with the sample present is then divided, point by point, by the background spectrum to give a percentage transmission, wherein the logarithm of the percentage transmission gives the absorbance spectrum. In an experimental setup for reflection, the probe is configured without a crystal tip. It is placed a distance from the tissue that is suitable for collection of reflectance data.

Preferably, a flexible fiber-optic cable comprising a mid-infrared-transmitting glass chalcogenide equipped with a MCT detector is coupled to a spectrometer. The fiber optic is preferably 1 to 2 meters in length and is transmissive over the infrared region of at least 400 to 4,000 $cm^{-1}$. A 5 mm diameter ZnS probe with a 1 mm region of surface contact can be attached to the end of the cable, thereby permitting sampling of 1 mm diameter sample areas. To minimize damage to the tissue, it is desirable to utilize a flat-ended ZnS crystal instead of the standard pointed design. The standard tip is a nominal two-bounce design, whereas the flat-ended design is a nominal three-bounce design. The optimum design will have the highest possible penetration depth on the flat face of the crystal, while avoiding the loss of light that will occur if an appreciable percentage of the rays exceeds the Brewster angle.

A host tissue in the context of the present invention includes tissue that naturally occurs in the body of a human or an animal, such as soft connective tissue, such as articular cartilage, meniscal cartilage, ligament, tendon and capsule, or mineralized tissue such as bone or teeth. The non-host material can be another tissue (such as a bone graft or allograft) or a synthetic material, such as a polymer, a synthetic bone substitute, a bone cement such as polymethyl methacrylate ("PMMA"), a metal or a ceramic.

For detection by ATR, the infrared radiation penetrates the surface of the region of interest (for example, the region suspected of containing a host tissue in intimate contact with a non-host material) to a depth of approximately up to 10 microns. For ATR, the probe is in contact (touches) the region of interest. For reflection, the probe is within a sufficient distance from the surface of the region of interest for detecting reflection (such distance could be a few centimeters from the surface of the region of interest).

Infrared radiation is analyzed in the present invention for at least one of peak height, peak area, frequency and chemometric parameters. The term "chemometrics" has been defined as follows:

"Chemometrics is the use of mathematical and statistical methods for handling, interpreting, and depicting chemical data." Malinowski E. R., (1991) *Factor Analysis in Chemistry: Second Edition*, page 1.

"The entire process whereby data (e.g., numbers in a table) are transformed into information used for decision making." Beebe K. R., Pell R. J., and M. B Seasholtz, (1998) *Chemometrics: A Practical Guide*, page 1.

"Chemometrics is a chemical discipline that uses mathematics, statistics and formal logic (a) to design or select optimal experimental procedures;

(b) to provide maximum relevant chemical information by analyzing chemical data; and (c) to obtain knowledge about chemical systems. Massart D. L., et al., (1997) *Data Handling in Science and Technology* 20 *A: Handbook of Chemometrics and Qualimetrics Part A*, page 1.

The analysis of the infrared radiation according to the present invention involves comparing at least one of peak height, peak area, frequency and chemometric parameters for one or both materials to established or pre-selected values, or the ratio for at least one of peak heights, peak area, frequencies and chemometrics for one or both materials.

One method of the present invention is to utilize an IFOP to discriminate between bone and at least one other compound or material (such as a compound or material in contact with a bone) whose signature IR spectrum are sufficiently different to be able to distinguish between them.

Figure 1:
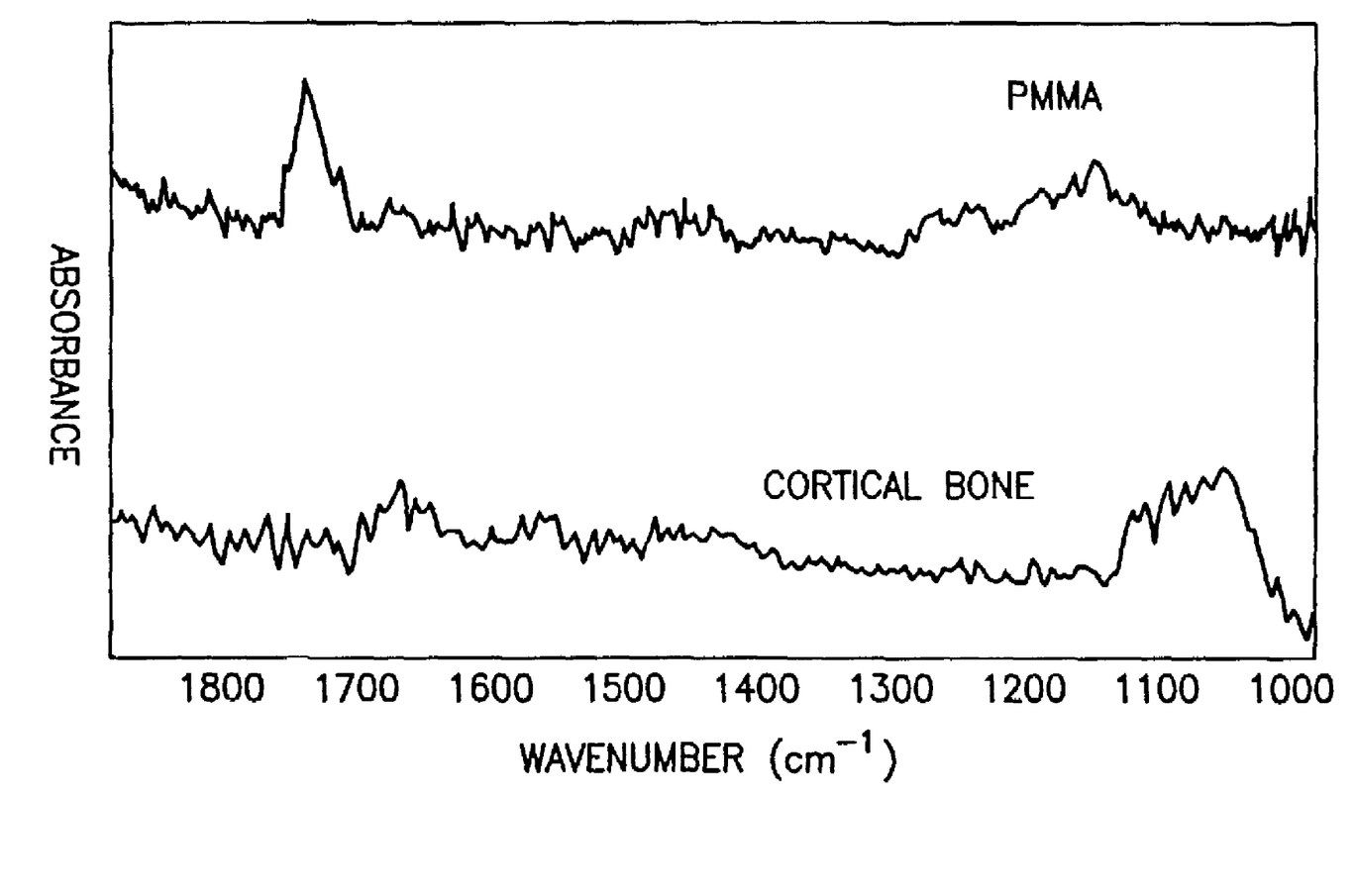
The drawing shows mid-infrared spectra of PMMA and bone. PMMA has a distinct absorbance band at approximately 1740 $cm^{-1}$. Bone displays a distinct absorbance at approximately 1030 $cm^{-1}$.

As an example of the application of the present invention would utilize the IFOP to discriminate between bone cement, usually comprised of polymethyl methacrylate (PMMA), and bone tissue in vivo by examination of the infrared spectrum of the material of interest. Prior to the present invention, other than visual examination, there was no method to discriminate between bone and other materials in contact with bone (such as bone cement) in vivo during surgical procedures. Although with direct observation one can often discriminate between such two materials, it can also at times be quite difficult to discriminate between the two materials. This is especially true in the femoral canal during revision total joint surgery, when visualization is limited. Specific IR signature absorbance bands arise from bone and PMMA (see the drawing), and differences in these bands can be used to identify these components. Discrimination of bone and PMMA would be carried out by the IFOP during surgical procedures such as revision of total joint replacements. The present invention thus provides a chemical basis by which it is possible to distinguish between these two materials in situ.

Another use of the present invention is to discriminate between bone and a metal or plastic implant surface in vivo. The infrared spectra of bone and a plastic, such as polyethylene, or a metal (no infrared absorbance) are sufficiently different such that these materials can be identified in vivo during surgical procedures.

Another method of the present invention involves a combination of a probe operative in the mid-infrared region or the near-infrared region of the EM for in situ sensing of the absorption of IR energy or of reflected TR energy, together with a removal system, such as an ablation, debridement or cutting system (e.g., an ultrasonic ablator or a laser). The ablator (such as sold by Misonix, Inc. of Farmingdale, N.Y., USA) or cutting instrument receives signals from the probe and would indicate with a LED when to ablate, or could be turned-off automatically by incoming IR signals. For example, ablation will be carried out only so long as the probe detects PMMA. Thus, the identification and removal of a non-host material are carried out in one step.

The use of an ultrasound or ultrasonic device is described in the following U.S. Patents, the entire disclosure of each of such U.S. Patents is hereby incorporated by reference herein: U.S. Pat. Nos. 5,516,043; 5,527,273; 6,063,050; 6,036,667 and 6,270,471.

As the removal device or ablator, it is preferred to use an ultrasonic device which by its nature is in physical contact with the surface of the region of interest (such as in detecting ATR). The ultrasonic device avoids the use of electromagnetic radiation such as in a laser. The ultrasonic device removes undesired material by vaporizing the material.

The present invention is also useful for cleaning surfaces where at least one substance or tissue has a clearly distinct and detectable IR spectrum. Examples are as follows: teeth and fillings; and cement between two materials, such as metal and bone.

In accordance with the present invention, resins or any other material that has a distinguishable infrared spectrum that are embedded in other materials can be examined. For example, pearls are often glued onto hollow metal (or other) receptacles. The excess glue can be ablated without touching the pearl if the ablator functions only when the infrared signal from the glue is detected.

In another example according to the present invention, impurities on surfaces of materials can be removed if at least one of the materials has a distinguishable infrared spectrum by actuating an ablator, cutter, carver or polisher when the appropriate infrared IR signal is given. That is, when either the host material or the impurity have at least one IR peak that is distinguishable from the other material, and the height or area of this peak, or the chemometric parameters of the IR spectrum is pre-selected to actuate the ablator, cutter, carver or polisher.

It will be appreciated that the instant specification is set forth by way of illustration and not limitation, and that various modifications and changes may be made without departing from the spirit and scope of the present invention.

What is claimed is:

1. A method of evaluating the surface of a material that has a distinguishable infrared spectrum comprising:

(a) positioning an infrared fiber optic probe to be in contact with a surface of a region of interest of a sample of a material selected from the group consisting of cartilage, ligament, tendon, capsule, bone and teeth, for detecting attenuated total reflectance or within a sufficient distance from the surface of the region for detecting reflection, (b) detecting mid-infrared or near-infrared radiation transmitted via attenuated total reflectance or reflection off of the surface of the sample of the material, (c) analyzing the infrared radiation from step (b) for at least one of peak height, peak area, frequency and chemometric parameters, and
(d) actuating a removal device when a signal from the infrared fiber optic probe is between pre-selected values for at least one of peak height, peak area, frequency and chemometric parameters for the sample of the material, to evaluate the surface of the material.

2. The method of claim 1, wherein attenuated total reflectance is detected.

3. The method of claim 1, wherein reflection is detected.

4. The method of claim 1, wherein the removal device is an ultrasonic ablator.

5. The method of claim 1, wherein the material is a cartilage which is selected from the group consisting of articular cartilage and meniscal cartilage.

6. A method of distinguishing between two materials comprising a first material and a second material that have different infrared spectra and separating or removing the first material from the second material comprising:
(a) positioning an infrared fiber optic probe to be in contact with a surface of a region of interest for detecting attenuated total reflectance or within a sufficient distance from the surface of the region for detecting reflection,
(b) detecting mid-infrared or near-infrared radiation transmitted via attenuated total reflectance or reflection off of the surface of the region of interest,
(c) analyzing the infrared radiation from step (b) for at least one of peak height, peak area, frequency and chemometric parameters for one or both materials, and
(d) actuating a removal device when a signal from the infrared fiber optic probe is between pre-selected values for (i) at least one of peak height, peak area, frequency and chemometric parameters for one or both materials, or (ii) a ratio for at least one of said peak height, peak area, frequency and chemometric parameters for one or both materials, to separate or remove the first material from the second material, for distinguishing between the two materials,
wherein the first material is selected from the group consisting of cartilage, ligament, tendon, capsule, bone and teeth, and wherein said second material is selected from the group consisting of a bone graft, an allograft and a synthetic material.

7. The method of claim 6, wherein attenuated total reflectance is detected.

8. The method of claim 6, wherein reflection is detected.

9. The method of claim 6, wherein the removal device is an ultrasonic ablator.

10. The method of claim 6, wherein said second material is a synthetic material which is selected from the group consisting of a polymer, a synthetic bone substitute, a bone cement, a metal and a ceramic.

11. The method of claim 10, wherein the synthetic material is a bone cement which is polymethyl methacrylate, and wherein the first material is bone.

12. A method of distinguishing between two materials comprising a first material and a second material that have different infrared spectra and separating or removing the first material from the second material comprising:
(a) positioning an infrared fiber optic probe to be in contact with a surface of a region of interest for detecting attenuated total reflectance or within a sufficient distance from the surface of the region for detecting reflection;
(b) detecting mid-infrared or near-infrared radiation transmitted via attenuated total reflectance or reflection off of the surface of the region of interest;
(c) analyzing the infrared radiation from step (b) for at least one of peak height, peak area, frequency and chemometric parameters for one or both materials, and
(d) actuating a removal device when a signal from the infrared fiber optic probe is between pre-selected values for (i) at least one of peak height, peak area, frequency and chemometric parameters of one or both materials, or (ii) a ratio for at least one of said peak height, peak area, frequency and chemometric paremeters for one or both materials, to separate or remove the first material from the second material, for distinguishing between the two materials,
wherein the first material is a tooth and the second material is a filling.

13. The method of claim 12, wherein attenuated total reflectance is detected.

14. The method of claim 12, wherein reflection is detected.

15. The method of claim 12, wherein the removal device is an ultrasonic ablator.

16. A method for discriminating between a host tissue and a nonhost material in vivo comprising:
(a) positioning an infrared fiber optic probe operative in the mid-infrared region or the near-infrared region of the electromagnetic spectrum to be in contact with a surface of a region of interest where it is considered that a host tissue selected from the group consisting of cartilage, ligament, tendon, capsule, bone and teeth is in intimate contact with a non-host material selected from the group consisting of a bone graft, an allograft and a synthetic material, for detecting attenuated total reflectance or within a sufficient distance from the surface of the region for detecting reflection,
(b) detecting mid-infrared radiation or near-infrared radiation penetrating the surface of the region and transmitted via attenuated total reflectance or reflection off of the surface of the region of interest, and
(c) analyzing the infrared radiation from step (b) for at least one of peak height, peak area, frequency and chemometric parameters for the host tissue, or the non-host material, or both the host tissue and the non-host material, and comparing at least one of peak height, peak area, frequency and chemometric parameters to established values for at least one of said peak height, peak area, frequency and chemometric parameters for the host tissue, or the non-host material, or both the host tissue and the non-host material, to detect the presence or absence of a non-host material, for discriminating between the host tissue and the non-host material.

17. The method of claim 16, wherein attenuated total reflectance is detected.

18. The method of claim 16, wherein reflection is detected.

19. The method of claim 16, wherein said non-host material is a synthetic material which is selected from the group consisting of a polymer, a synthetic bone substitute, a bone cement, a metal and a ceramic.

20. The method of claim 19, wherein the synthetic material is a bone cement, which is polymethyl methacrylate, and wherein the host tissue is bone.

21. A method for separating a host tissue in intimate contact with a non-host material comprising:

(a) positioning an infrared fiber optic probe operative in the mid-infrared region or the near-infrared region of the electromagnetic spectrum in combination with a removal device, the removal device being capable of receiving signals from the infrared fiber optic probe, to be in contact with a surface of a region of interest where it is considered that a host tissue selected from the group consisting of cartilage, ligament, tendon, capsule, bone and teeth is in intimate contact with a non-host material selected from the group consisting of a bone graft, an allograft and a synthetic material, for detecting attenuated total reflectance or within a sufficient distance from the surface of the region for detecting reflection, (b) detecting with the infrared fiber optic probe mid-infrared radiation or near-infrared radiation penetrating the surface of the region and transmitted via attenuated total reflectance or reflection off of the surface of the region of interest, (c) analyzing the infrared radiation from step (b) for at least one of peak height, peak area, frequency and chemometric parameters for the host tissue, the non-host material or both of the host tissue and the non-host material, and (d) actuating the removal device when a signal from the infrared fiber optic probe is between pre-selected values for (i) at least one of peak height, peak area, frequency and chemometric parameters for one or both of the host tissue and the non-host material, or (ii) a ratio for at least one of said peak height, peak area, frequency and chemometric parameters for one or both of the host tissue and the non-host material.

22. The method of claim 21, wherein attenuated total reflectance is detected.

23. The method of claim 21, wherein reflection is detected.

24. The method of claim 21, wherein the removal device is an ultrasonic ablator.

25. The method of claim 21, wherein said non-host material is a synthetic material which is selected from the group consisting of a polymer, a synthetic bone substitute, a bone cement, a metal and a ceramic.

26. The method of claim 25, wherein the synthetic material is a bone cement which is polymethyl methacrylate, and wherein the host tissue is bone.

27. A method of measuring the thickness of a substrate in contact with a surface material comprising:
(a) positioning an infrared fiber optic probe operative in the mid-infrared region or the near-infrared region of the electromagnetic spectrum to be in contact with a surface of a region of interest where it is considered that a surface material selected from the group consisting of cartilage, ligament, tendon, capsule, bone and teeth is in intimate contact with a substrate selected from the group consisting of a bone graft, an allograft and a synthetic material, for detecting attenuated total reflectance or within a sufficient distance from the surface of the region for detecting reflection, (b) detecting mid-infrared radiation or near-infrared radiation penetrating the surface of the region and transmitted via attenuated total reflectance or reflection off of the surface of the region of interest, and (c) analyzing the intensity of the infrared radiation from step (b) for at least one of peak height, peak area, frequency and chemometric parameters to measure the thickness of the substrate.

28. The method of claim 27, wherein attenuated total reflectance is detected.

29. The method of claim 27, wherein reflection is detected.

30. The method of claim 27, wherein said substrate is a synthetic material which is selected from the group consisting of a polymer, a synthetic bone substitute, a bone cement, a metal and a ceramic.

31. The method of claim 30, wherein the synthetic material is a bone cement which is polymethyl methacrylate, and wherein the surface material is bone.

* * * * *